(12) United States Patent
Banowetz et al.

(10) Patent No.: US 10,031,331 B2
(45) Date of Patent: Jul. 24, 2018

(54) INSPECTION APPARATUS GUIDE SYSTEM

(71) Applicant: General Electric Company, Schenectady, NY (US)

(72) Inventors: Daniel Lawrence Banowetz, Glenville, NY (US); Jordan Christopher Baker, Canajoharie, NY (US); Thomas James Batzinger, Burnt Hills, NY (US); Anthony James George, Clifton Park, NY (US); Ronald Irving Longwell, Boynton Beach, FL (US); Matthew Peter Scoffone, Greenville, SC (US); Daniel David Soloway, Greenville, SC (US)

(73) Assignee: General Electric Company, Schenectady, NY (US)

( * ) Notice: Subject to any disclaimer, the term of this patent is extended or adjusted under 35 U.S.C. 154(b) by 823 days.

(21) Appl. No.: 13/937,974

(22) Filed: Jul. 9, 2013

(65) Prior Publication Data
US 2015/0013791 A1    Jan. 15, 2015

(51) Int. Cl.
*G02B 23/16* (2006.01)
*G02B 23/24* (2006.01)
(Continued)

(52) U.S. Cl.
CPC ....... *G02B 23/2476* (2013.01); *G01N 21/952* (2013.01); *G02B 23/16* (2013.01);
(Continued)

(58) Field of Classification Search
CPC ............... G02B 23/2476; G02B 23/16; G02B 23/2492; G01N 21/954
(Continued)

(56) References Cited

U.S. PATENT DOCUMENTS 3,246,521 A * 4/1966 Humphrey ............... G01K 1/14
374/148
3,690,775 A    9/1972 Cousins
(Continued)

FOREIGN PATENT DOCUMENTS

| CN | 2427793 Y | 4/2001 |
|----|-----------|--------|
| CN | 1442683 A | 9/2003 |

(Continued)

OTHER PUBLICATIONS

European Search Report and opinion in connection with corresponding EP Application No. 14175769.0 dated Nov. 6, 2014.
(Continued)

*Primary Examiner* — Daniel S Larkin
*Assistant Examiner* — Alexander Mercado
(74) *Attorney, Agent, or Firm* — Ernest G. Cusick; Hoffman Warnick LLC

(57) ABSTRACT

A valve body in a passage of a housing connected to a through hole in a sealed machine casing can allow an inspection apparatus into an interior of the casing when open, and prevents fluid flow through the passage when closed. Seals can engage the inspection apparatus to prevent fluid flow through the passage during inspection or inspection apparatus movement. A guide conduit in the casing can include branches and can guide the inspection apparatus to multiple inspection sites. Guide marks can identify the branches to assist with navigation within the casing.

15 Claims, 12 Drawing Sheets

(51) Int. Cl.
  *H02K 15/00* (2006.01)
  *G01N 21/952* (2006.01)
  *H02K 5/12* (2006.01)

(52) U.S. Cl.
  CPC ......... *G02B 23/2492* (2013.01); *H02K 15/00* (2013.01); *H02K 5/12* (2013.01); *Y10T 137/8359* (2015.04)

(58) Field of Classification Search
  USPC .......................................................... 73/431
  See application file for complete search history.

(56) References Cited

U.S. PATENT DOCUMENTS

| | | |
|---|---|---|
| 3,778,170 A | 12/1973 | Howell et al. |
| 3,917,432 A | 8/1975 | Feuerstein et al. |
| 4,011,017 A | 3/1977 | Feuerstein et al. |
| 4,575,185 A | 3/1986 | Wentzell et al. |
| 5,354,990 A | 10/1994 | Dankworth et al. |
| 5,382,856 A | 1/1995 | Keck et al. |
| 5,451,772 A | 9/1995 | Narendran |
| 5,531,664 A | 7/1996 | Adachi et al. |
| 5,681,260 A | 10/1997 | Ueda et al. |
| 5,702,345 A | 12/1997 | Wood et al. |
| 5,764,823 A | 6/1998 | Shapanus et al. |
| 5,867,976 A | 2/1999 | Ziegler, Jr. |
| 6,452,294 B1 | 9/2002 | Vandervort et al. |
| 6,794,773 B2 | 9/2004 | Jordan et al. |
| 7,422,559 B2 | 9/2008 | Kehoskie et al. |
| 7,458,768 B2 | 12/2008 | Dube et al. |
| 7,662,091 B2 | 2/2010 | Bagley et al. |
| 7,717,666 B2 | 5/2010 | Roney, Jr. et al. |
| 8,047,769 B2 | 11/2011 | Ballard, Jr. |
| 8,076,909 B2 | 12/2011 | Diatzikis et al. |
| 8,139,905 B1 | 3/2012 | Bazzone |
| 8,246,298 B2 | 8/2012 | Wilson |
| 8,275,558 B2 | 9/2012 | Reed et al. |
| 8,362,661 B2 | 1/2013 | DeBlock et al. |
| 2004/0006448 A1 | 1/2004 | Penza |
| 2004/0019252 A1* | 1/2004 | Hirata ................ G02B 23/2476 600/114 |
| 2008/0079933 A1 | 4/2008 | Fukami et al. |
| 2009/0278924 A1 | 11/2009 | Heyworth et al. |
| 2010/0076703 A1 | 3/2010 | Twerdochlib |
| 2011/0018483 A1 | 1/2011 | Koste et al. |
| 2012/0026482 A1 | 2/2012 | Dailey |
| 2012/0075633 A1 | 3/2012 | Xia et al. |
| 2012/0154821 A1 | 6/2012 | Koste et al. |

FOREIGN PATENT DOCUMENTS

| | | |
|---|---|---|
| CN | 102062738 A | 5/2011 |
| CN | 102165293 A | 8/2011 |
| KR | 100962521 B1 | 6/2010 |
| KR | 20120033293 A | 4/2012 |
| WO | 2011110240 A1 | 9/2011 |

OTHER PUBLICATIONS

Creel et al., "Monitoring of Generator Stator End-Winding Vibration How Reliable are Existing Monitoring Systems?", Brush Aftermarket Gms, pp. 1-9, Jan. 2000.

Unofficial English Translation of Chinese Office Action issued in connection with corresponding CN Application No. 201310124986.9 dated Dec. 25, 2015.

Office Action dated Feb. 19, 2018 for European Application 14175769.0 filed Jul. 14, 2015; pp. 4.

* cited by examiner

INSPECTION APPARATUS GUIDE SYSTEM

BACKGROUND OF THE INVENTION

The disclosure relates generally to inspection of machine components, and more particularly to inspection of components of a dynamoelectric machine, such as an electric generator, at least partly immersed in a fluid in a sealed chamber, such as a sealed casing.

Dynamoelectric machines can include sections that are difficult to access, but that include components that require inspection. Some such machines include areas that are immersed in a fluid or otherwise require isolation from atmosphere, which further impedes access for inspection and/or maintenance. For example, some electric generators include a casing filled with a coolant in which the rotor of the generator rotates. The coolant typically must be kept in the casing because it would be contaminated should air enter the casing or might have an effect on surroundings should it escape. This is particularly true of hydrogen cooled generators, where hydrogen gas fills the generator casing, usually under pressure, to cool the windings and/or magnets and/or other parts of the generator.

To inspect components in such a machine typically requires shutting down the machine, draining the fluid, and disassembling the machine at least as far as inspection can be performed, reassembling the machine, and recharging the casing with fluid before restarting the machine. In the case of hydrogen cooled generators, care must be used to contain and/or dilute the hydrogen to avoid fire/explosion hazard during draining and recharging of the casing. The process can be time consuming and expensive.

The problem of inspection that can require time consuming and/or expensive disassembly and reassembly is not unique to dynamoelectric machines, and, as a result, inspection apparatus have been developed to inspect many devices, machines, and/or installations. Of particular interest with respect to embodiments of the invention disclosed herein, borescopes are used to inspect portions and/or components of turbomachines that would otherwise require disassembly of the machines. A typical borescope includes a head on the end of an elongated support structure. The head can capture an image that can be viewed by a user. For example, the head can include a lens that can transmit the image to a viewer or eyepiece or the like via fiber optic cable extending through the support structure. Alternatively, the head can include a camera that can transmit a captured image to a display via signals carried by an electrical conductor in the support structure and/or electromagnetic radiation. The support structure is typically a tube or concentric tubes in which optical fiber, electrical conductors, cables, and/or other components extend from a control box to the head. Rigid borescopes typically employ a tube that is resistant to bending. Flexible borescopes typically include a flexible tube, which can be made from a tube of flexible material and/or can be a composite of joined segments of material. Controls on the control box can be used to adjust the orientation of the head and/or tube, to activate lighting, and/or employ other features of the borescope.

To accommodate inspection with borescopes, turbomachine casings can include a plurality of access ports sealed with borescope plugs or the like to seal the access ports when no borescope is present and/or between inspections and/or uses of the ports. In addition, borescope mounts have been used to support and/or enhance operation of borescopes, such as by allowing a borescope to swivel in place to increase a viewable area, and/or using a guide tube to conduct a borescope through layers of casings or the like to an inspection site. However, the machines in which these are installed and/or used can typically be depressurized and/or shut down to allow swapping out of a port cover for a borescope or the like with relative ease and without significant passage of fluid through the port. Thus, these solutions typically are not suited for use in a machine whose casing is sealed and contains fluid that should be kept within the casing, particularly pressurized gas, even when shut down.

BRIEF DESCRIPTION OF THE INVENTION

Embodiments of the invention disclosed herein may take the form of an inspection apparatus guide system with a housing configured at a first end thereof for attachment to a casing. The housing can include a main passage therethrough that can be configured for communication with a first through hole in the casing. In addition, the main passage can be sized to receive an inspection apparatus extendible therethrough. A valve body can be mounted in the housing so that an outboard portion of the main passage lies between the valve body and a second end of the housing. In a first position, the valve body can seal the outboard portion of the main passage from the interior of the casing, while in a second position, the valve body opens the main passage to the interior of the casing. A first seal can be mounted in the housing so as to project into the main passage and can be located farther from the casing than the valve body is. An inner periphery of the first seal can be smaller than an outer periphery of the inspection apparatus so that the first seal can sealingly engage the inspection apparatus, thereby substantially preventing passage of fluid between the inner periphery of the first seal and the outer periphery of the inspection apparatus.

Embodiments of the invention may also take the form of an inspection apparatus guide system for facilitating inspection of an interior of a sealed casing of a machine. A guide conduit can extend from a first through hole in the sealed casing to an inspection site inside the casing. Both the guide conduit and the first through hole can be sized to allow passage of an inspection apparatus, as can a main passage of a housing configured for attachment to the sealed casing. When the casing is attached to the sealed casing, at least an inboard end of the main passage can be aligned with the first through hole. The main passage can be spanned by a valve body supported in the housing, the valve body having a first position in which the valve body can substantially prevent fluid communication between an interior of the sealed casing and a portion of the main passage outboard of the valve body. The valve body can have a second position in which the valve body can allow fluid communication between the interior of the sealed casing and the portion of the main passage outboard of the valve body. A first seal supported in the housing outboard of the valve body can project into the main passage, the first seal having an inner periphery that is smaller than an outer periphery of the inspection apparatus so that the first seal can engage the inspection apparatus in an interference fit when the inspection apparatus extends through the main passage.

In addition, embodiments of the invention disclosed herein can take the form of an inspection apparatus guide system for facilitating inspection of a sealed casing of a machine. A housing can include a main passage that can be configured to allow passage of an inspection apparatus selectively extendible therethrough. A retainer can be mounted in the housing at an outboard end of the housing opposite the inboard end. The retainer can selectively engage the inspection apparatus in an interference fit and can selectively retain the inspection apparatus against motion relative to the retainer. A valve body supported in the housing can seal an outboard portion of the main passage between the valve body and the outboard end of the housing against fluid communication with an interior of the sealed casing in a first position of the valve body. In a second position of the valve body, the valve body can open the outboard portion of the main passage to fluid communication with the interior of the casing.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWING

These and other features of the disclosure will be more readily understood from the following detailed description of the various aspects of the invention taken in conjunction with the accompanying drawings that depict various aspects of the invention.

Figure 1:
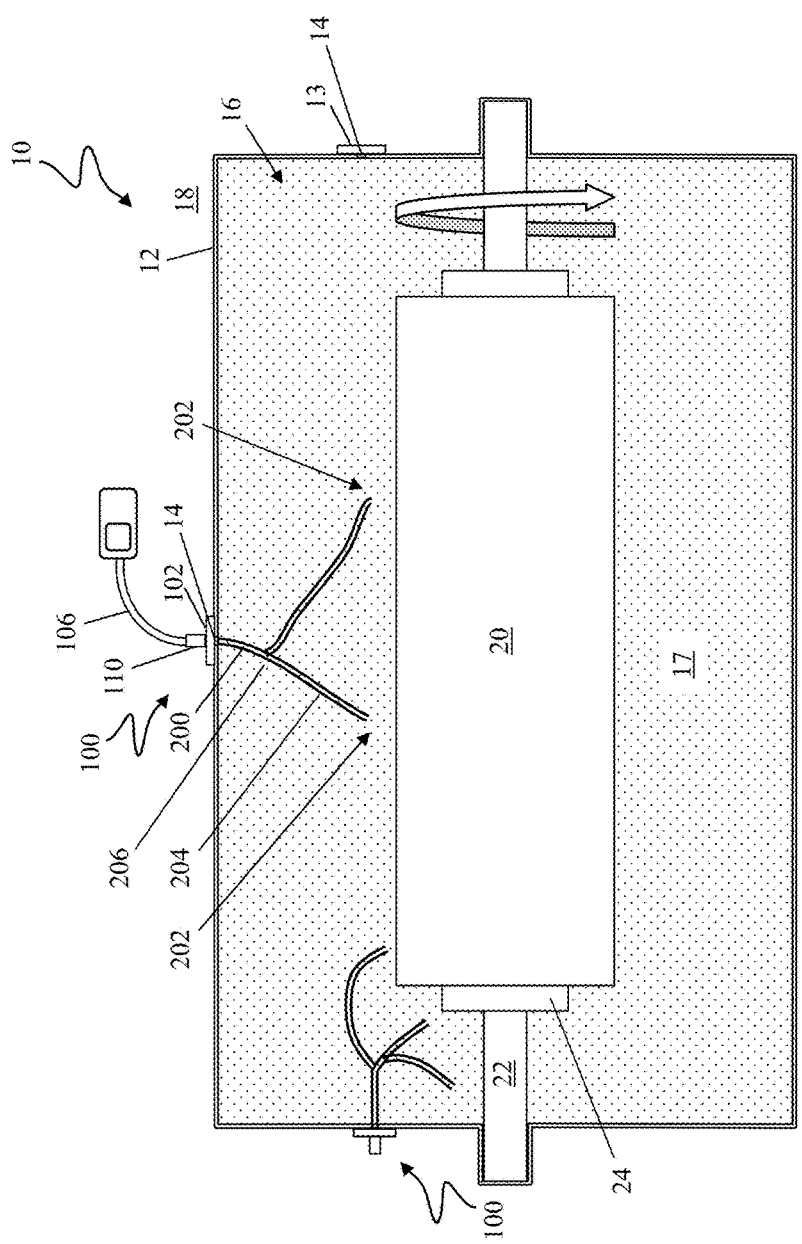
FIG. 1 shows a schematic longitudinal cross sectional diagram of a machine with which an inspection apparatus guide system according to embodiments of the invention disclosed herein can be used.

It is noted that the drawings may not be to scale. The drawings are intended to depict only typical aspects of the invention, and therefore should not be considered as limiting the scope of the invention. In the drawings, like numbering represents like elements between the drawings. The detailed description explains embodiments of the invention, together with advantages and features, by way of example with reference to the drawings.

DETAILED DESCRIPTION OF THE INVENTION

As used herein, to "sealingly engage" means to engage in such a manner that fluid flow across a point, line, and/or plane of engagement between two parts and/or objects is substantially prevented. Also as used herein, a "dynamic seal" is a seal that allows a part and/or object the seal engages to move relative to the seal while sealingly engaging the part and/or object. Likewise, a "static seal" is a seal that substantially prevents a part and/or object the seal engages from moving relative to the seal. "Inboard" as used herein means closer to or toward a referential object and/or portion thereof, while "outboard" means farther or away from a referential object and/or portion thereof. Thus, if a housing is attached to a casing, an end of the housing closest to the casing can be said to be an inboard end, while an end of the housing farthest from the casing can be said to be an outboard end, and if a first component in the housing is closer to the casing than a second component is, the first object can be said to be inboard of the second component, while the second component can be said to be outboard of the first component.

Aspects of the invention provide an inspection apparatus guide system that can allow inspection of components inside a sealed machine casing without first draining fluid from within the casing and/or disassembling the casing and/or machine. The system can include a housing mounted over a through hole in the casing, such as an access port with which a passage in the housing can be aligned. An inspection apparatus, such as a borescope, can be inserted from an exterior of the casing into the interior of the casing through the passage and the through hole. Seals mounted in the housing can engage the inspection apparatus to reduce and/or prevent fluid exchange between the interior and exterior of the casing via the passage. A valve in an inboard portion of the passage ordinarily seals an outboard portion of the passage against fluid communication with the interior of the casing, but can be opened to allow the inspection apparatus to pass into the casing. A guide conduit or tube can be included inside the casing to aid in navigation to an inspection site within the casing, and the guide conduit can include branch points from which branches can extend to respective inspection sites. Guide marks can also be included on internal surfaces of the guide conduit at or near the branch points to further aid in navigation. To inspect, a user can insert the inspection apparatus into the passage just past a seal, open the valve, and extend the inspection apparatus into the casing, particularly through the guide conduit. Using the guide marks, the user can extend the inspection apparatus to a desired inspection site and conduct an inspection. A retainer can be included so that when the inspection apparatus has reached a desired inspection site, the retainer can be tightened to hold the inspection apparatus in place and can also be or act as a seal. The retainer can be disengaged to allow the inspection apparatus to be removed and/or extended to another inspection site. When the inspection apparatus is to be removed, the user withdraws the inspection apparatus just past the valve, closes the valve, and removes the inspection apparatus from the passage.

FIG. 1 is a schematic cross sectional view of a machine 10 with which a guide system 100 for an inspection apparatus 106, such as a borescope, can be used according to embodiments of the invention disclosed herein. As seen in FIG. 1, machine 10 can include a casing 12 bearing one or more access port covers 13 that cover and seal one or more through holes 14, such as access ports. An interior 16 of casing 12 can include and/or be filled with a fluid 17 that can be substantially prevented from escaping to an exterior 18 of casing 12 by known sealing arrangements, including access port covers 13. Such sealing arrangements can also prevent entry of air into interior 16, which could contaminate fluid 17 and/or have other undesirable effects. Casing 12 can support and/or house and/or protect machine components, such as first, second and third components 20, 22, 24. Where machine 10 is a dynamoelectric generator, fluid 17 can be hydrogen at a pressure greater than a pressure present in exterior 18, such as ambient atmospheric pressure. In addition, first component 20 can be a rotor supported by second component 22, which can be a shaft, and third component 24 can be a connector ring, end windings, or other component of a dynamoelectric generator. It should be understood that FIG. 1 is schematic in nature and that the components shown therein may not be to scale and/or may differ in layout.

In the schematic example of FIG. 1, guide system 100 for an inspection apparatus 106 according to embodiments of the invention disclosed herein is shown attached to casing 12 over a first through hole 14, such as an access port, that is sized to allow inspection apparatus 106 to pass therethrough. In the example shown, guide system 100 can include a housing 110 attached to casing 12, such as via a connector 102. Housing 110 can include a passage therethrough, discussed below, aligned with first through hole 14 at an inboard or casing end of housing 110 and sized to allow passage of inspection apparatus 106 through housing 110 and first through hole 14 into casing 12. A guide conduit or tube 200 in interior 16 of casing 12 can be aligned with first through hole 14 and can extend to an inspection point 202. Branches or branch conduits 204 can extend from one or more branch points 206 in guide conduit 200 to provide access to one or more additional inspection points 202. Each inspection point 202 can be a location within casing 12 from which one or more components 20, 22, 24 can be inspected after inserting inspection apparatus 106, such as a borescope tube, through housing 110 and guide conduit 200 and/or branch conduit(s) 204 so that an end of inspection apparatus 106 reaches inspection site 202. In embodiments, multiple guide systems 100 can be deployed and/or installed so that a single viewing apparatus 106 can be used with one guide system 100, removed, and used with one or more other guide systems 100 on a particular machine 10 or on other machines.

Connector 102, inasmuch as ways to attach an item to an object like casing 12 are well known, designates any suitable collection of parts, fasteners, adhesive, welds, and/or any other elements as may be used in the art to attach housing 110 to casing 12. However, some examples of connector 102 are included in FIGS. 3 and 4. Connector 102 can include a seal, such as a gland seal, O-ring, and/or other seal arrangement. Thus, as a non-limiting example seen in FIG. 3, an end face of housing 110 can support a seal 103, such as an O-ring, in a substantially annular groove 104. An externally-threaded projection 105 from the inboard end of housing 110 can include threads 107 that can interact with corresponding threads 108 on an inner periphery of first through hole 14 so that, as housing 110 is screwed into first through hole 14 via projection 105, seal 103 can be engaged between the inboard end of housing 110 and casing 12. Another non-limiting example is seen in FIG. 4, where seal 103 is mounted in a groove 104 of an end face of a flange 109 of housing 110, and casing 12. When flange 109 is attached to casing 12, such as with bolts 111, seal 103 can be engaged between the end face of flange 109 and casing 12. Alternatively, a mounting plate, a mounting ring, and/or other part could be added to attach housing 110 to casing 12 to overlie first through hole 14, including seals such as might have been used with cover 13. Additional components and/or techniques that could be used can include, but are not limited to, screws, bolts, rivets, cables, and/or other mechanical, chemical, and/or thermally-based fasteners.

Figure 2:
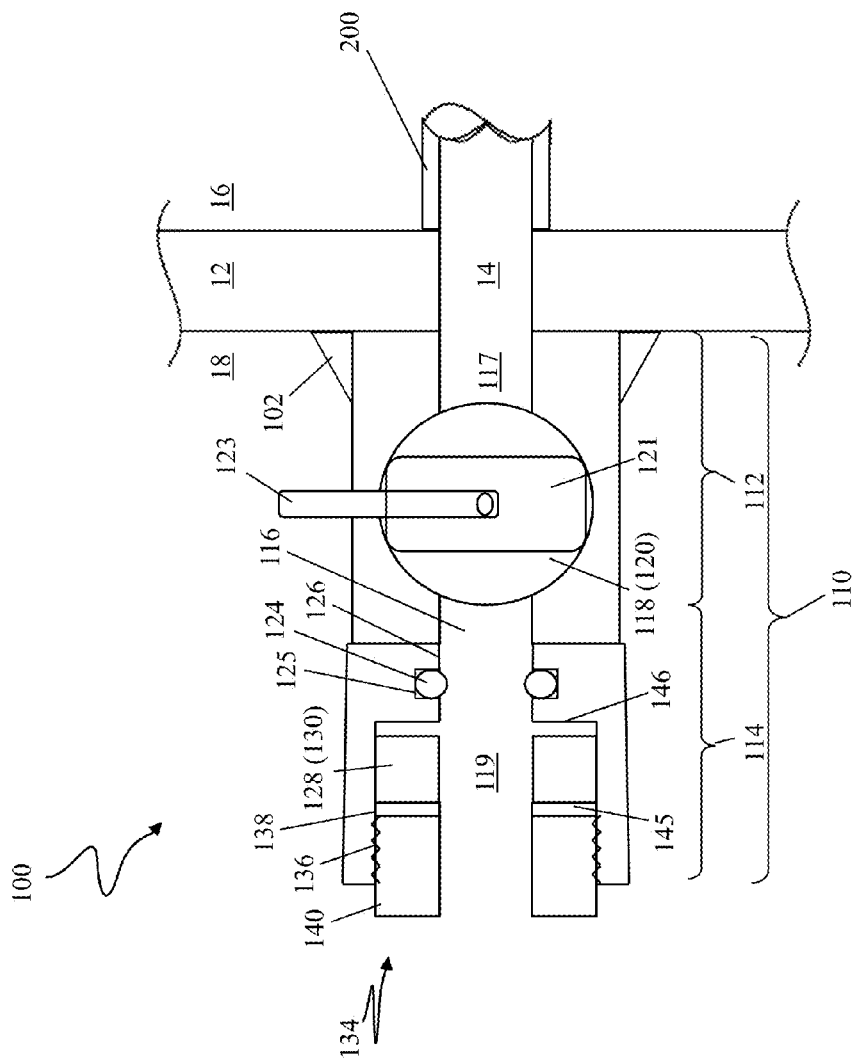
FIG. 2 shows a schematic cross sectional diagram of a first example of an inspection apparatus guide system according to embodiments of the invention disclosed herein in a first state.
Figure 3:
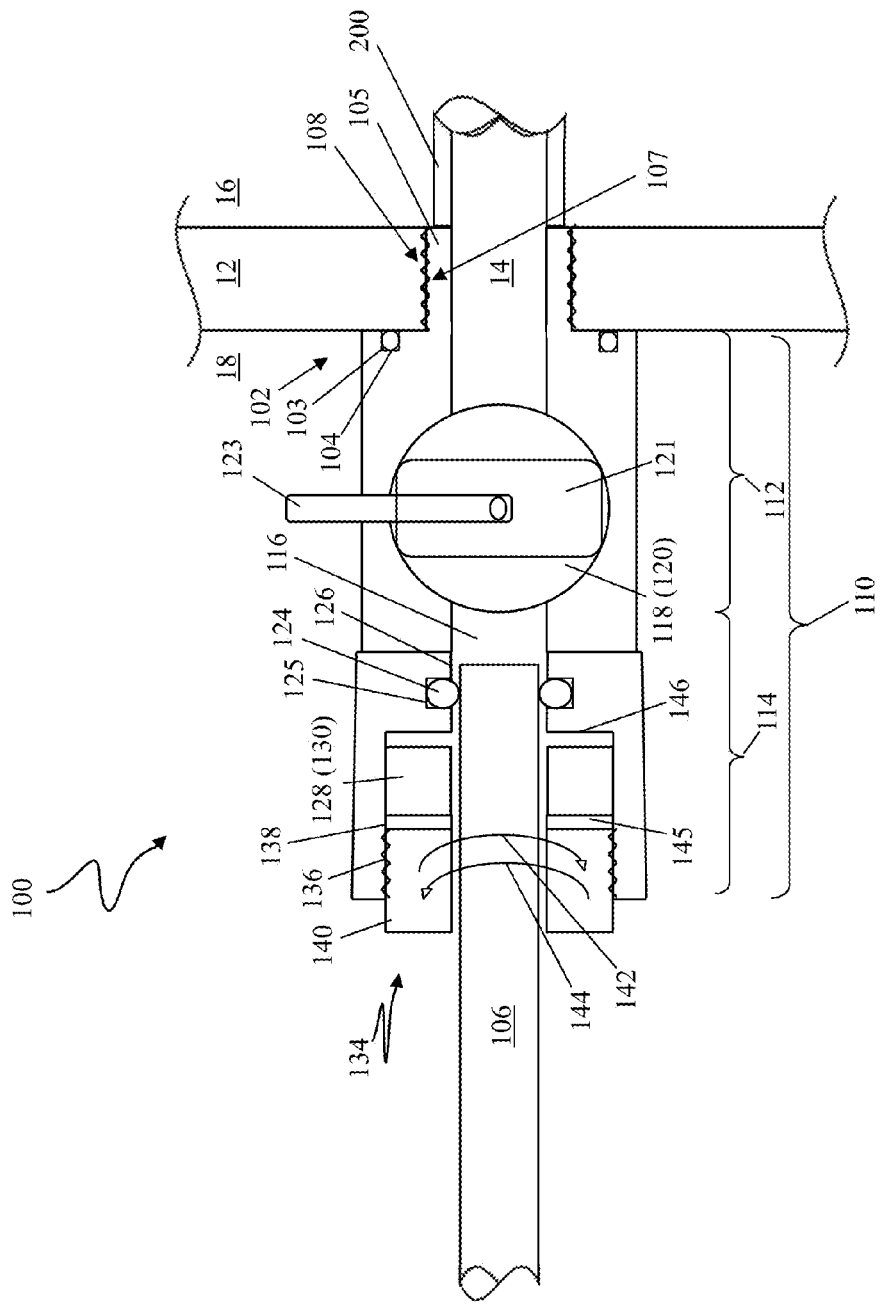
FIG. 3 shows a schematic cross sectional diagram of the first example of an inspection apparatus guide system according to embodiments of the invention disclosed herein in a second state.
Figure 4:
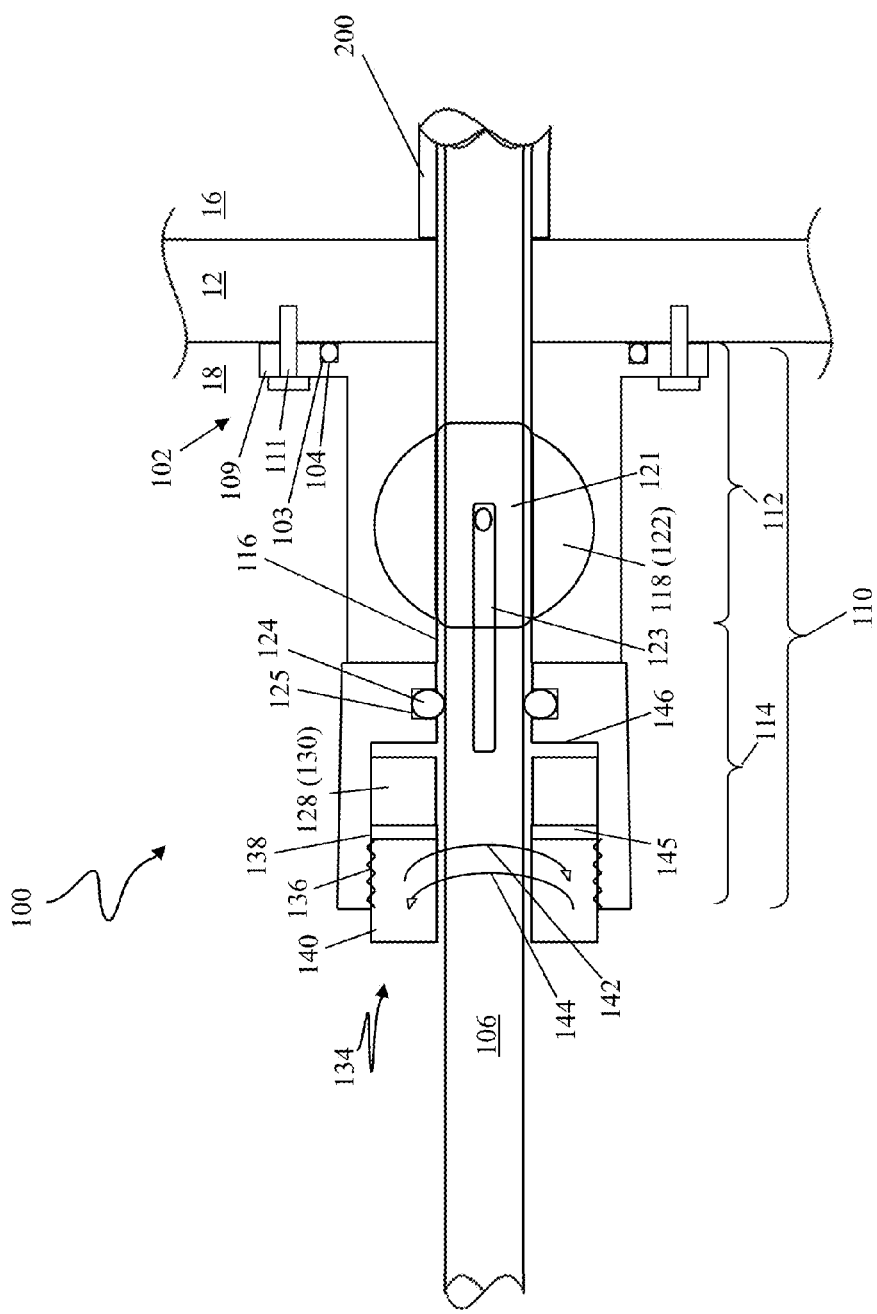
FIG. 4 shows a schematic cross sectional diagram of the first example of an inspection apparatus guide system according to embodiments of the invention disclosed herein in a third state.
Figure 5:
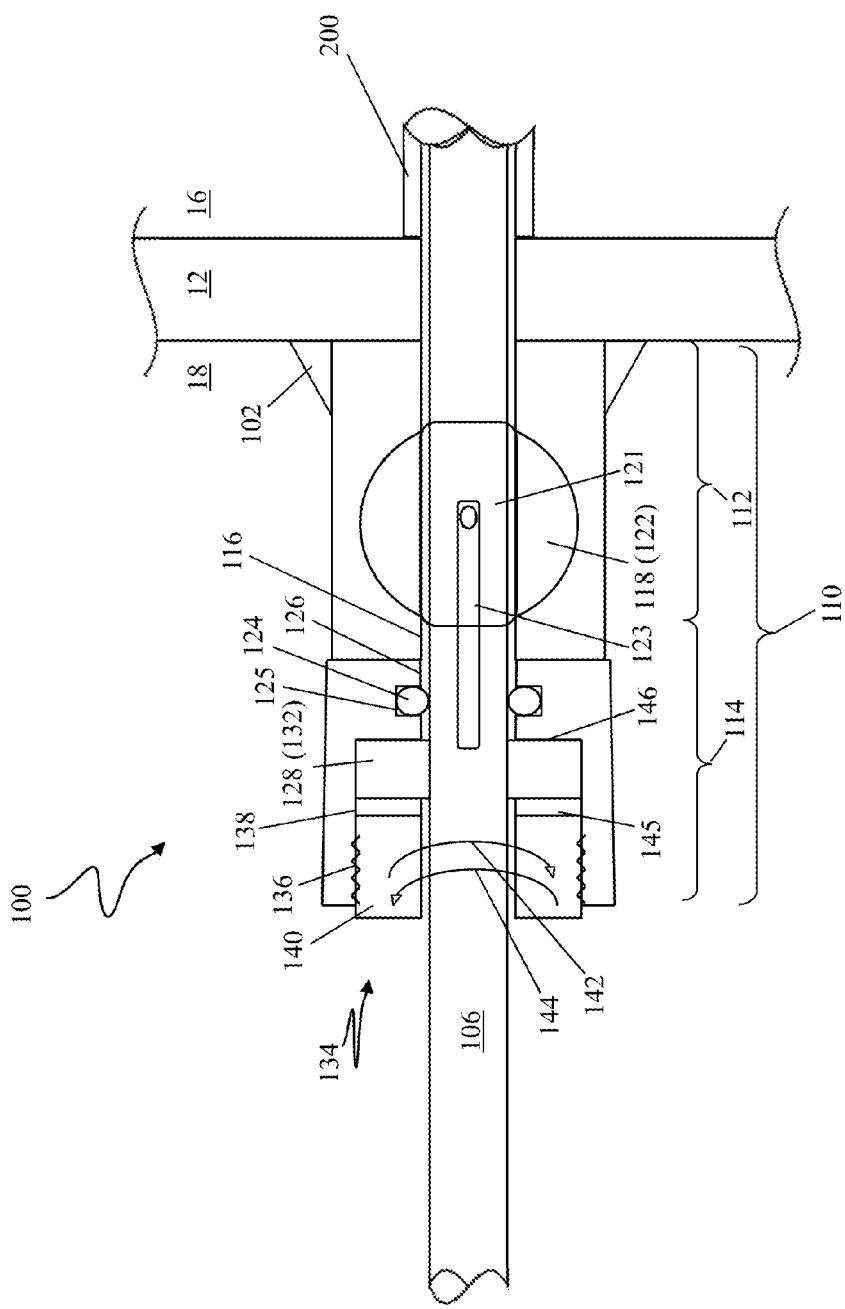
FIG. 5 shows a schematic cross sectional diagram of a first example of an inspection apparatus guide system according to embodiments of the invention disclosed herein in a fourth state.

FIGS. 2-5 show a more detailed first example of a guide system 100 according to embodiments of the invention disclosed herein attached to casing 12 and in various states as will be described. In FIG. 2, the first example of guide system 100 is shown as it might be between inspections, while FIG. 3 shows the first example of guide system 100 during an initial insertion or a final removal of inspection apparatus 106, FIG. 4 shows the first example of guide system 100 in an intermediate state with inspection apparatus 106 extending therethrough, and FIG. 5 shows the first example of guide system 100 as it might appear when inspection apparatus 106 has reached an inspection site 202 inside casing 12.

In the examples shown in FIGS. 2-5, a main passage 116 can extend through housing 110 with at least a portion of main passage 116 aligned with first through hole 14. In embodiments, housing 110 can be substantially cylindrical and main passage 116 can be a substantially cylindrical axial bore therein with a diameter larger than that of inspection apparatus 106, which can be a borescope tube. Housing 110 can be formed from any suitable material in any suitable fashion, and main passage can be formed therein using any suitable technique. For example, housing 110 can be cast or machined from a metal or metal alloy, which can include aluminum, iron, steel, and/or other metals and/or additives as may be suitable and/or desired. Main passage 116 can be formed as part of casting, extruding, and/or machining of housing 110, and/or can be formed by machining after formation of housing 110.

As shown in FIGS. 2-5, a valve body 118 or the like can be mounted in housing 110 so as to at least span or lie across main passage 116 and can include a bore 121 sized to allow passage of inspection apparatus 106 when valve body 118 is in an open position. With particular reference to FIG. 2, valve body 118 effectively divides housing 110 into an inboard portion 112 and an outboard portion 114, a dividing line of which for the purposes of description is arbitrarily regarded as extending perpendicular to a longitudinal axis of main passage 116 from an outboard edge of valve body 118. In addition, again with particular reference to FIG. 2, valve body 118 effectively divides main passage into an inboard portion 117 extending from an inboard end of valve body 118 toward casing 12, and an outboard portion 119 extending from the outboard edge of valve body 118 away from casing 12. Valve body 118 can be placed as close to casing 12 as is feasible and/or suitable and/or convenient. Housing 110 can include formations to support valve body 118, such as opposed recesses about main passage 116. Valves including valve bodies of these types are well understood, so details of mounting and arranging components thereof are not discussed in detail herein, since valve body 118 can be mounted with appropriate seals, bearings, bushings, and/or actuators as would be known by one of ordinary skill in the art to enable its function in main passage 116, which can include preventing fluid flow past valve body 118 when closed and allowing inspection apparatus 106 to pass when open, as will be described below.

In the first example of FIG. 2, and with additional reference to FIGS. 3-5, valve body 118 is shown as having a circular cross section with bore 121 being a diametral bore. In this example, therefore, valve body 118 can be cylindrical or can be a substantially spherical ball valve body and an actuator, such as a lever or handle 123, can be attached to valve body 118 to open and close valve body 118 by rotating valve body 118 about a central axis perpendicular to a longitudinal axis of bore 121. Whatever shape valve body 118 has, it can be formed, mounted, and/or actuated as is known in the valve arts so that, in a first or closed position 120 (FIGS. 2-3), a longitudinal axis of bore 121 is substantially perpendicular to a longitudinal axis of main passage 116, and, in a second or open position 122 (FIGS. 4-5), the longitudinal axis of bore 121 is coaxial with the longitudinal axis of main passage 116. Thus, in first position 120 (FIGS. 2-3), outboard portion 119 (FIG. 2) is sealed from fluid communication with inboard portion 117 (FIG. 2) and casing interior 16, and in second position 122 (FIGS. 4-5), bore 121 connects inboard and outboard portions 117, 119 (FIG. 2), opening main passage 116 to fluid communication with casing interior 16. In addition, in first position 120 (FIGS. 2-3), valve body 118 can prevent passage of inspection apparatus 106, but in second position 122 (FIGS. 4-5), valve body 118 can allow passage of inspection apparatus 106.

As noted above, valve body 118 can take any suitable shape and/or form, so long as main passage 116 can be blocked or sealed, but also opened to allow inspection apparatus 106 to pass therethrough. As a non-limiting example of another shape for valve body 118, valve body 118 could be a sliding plate with a suitably sized through hole and arranged so that main passage 116 is blocked until the valve body is moved so that the through hole is coaxial with main passage 16. In addition, while main passage 116 and housing 110 have been described as being cylindrical, any other shape could be used for either part so long as inspection apparatus 106 can be accommodated and first through hole 14 can be covered. As a non-limiting example, main passage 116 could have a rectangular cross section sized so that inspection apparatus 106 can pass therethrough, and/or housing 110 could have a hexagonal cross section. It should also be noted that, in some instances, fluid may be allowed to move from interior 16 to exterior 18 or from exterior 18 to interior 16, depending on the particular fluid contained in casing 12, its properties as might regard its effects on personnel and/or objects around casing 12, and/or an effect of air entering casing 12, so that a one-way seal might be used in some instances. From a practical standpoint, particularly where pressurized hydrogen is contained in casing 12, it may be extremely difficult to prevent all leakage of hydrogen through main passage 116, but valve body 118 can at least reduce leakage to an acceptable level in embodiments, which level may vary depending on particular implementations of guide system 100.

Housing 110, particularly outboard portion 114 of housing 110, can support a first seal 124 farther from casing 12 than valve body 118 is and so that first seal 124 can project into main passage 116. For example, where main passage 116 is substantially cylindrical, first seal 124 can be an elastomeric, substantially annular seal, such as an O-ring, supported in a substantially annular groove 125 in housing 110 that can extend from an inner surface 126 of main passage 116 into housing 110. First seal 124 can be sized so that it can sealingly engage inspection apparatus 106, by which is meant that when inspection apparatus 106 is inserted through first seal 124, a substantially fluid-tight engagement results that substantially prevents fluid passing between first seal 124 and the outer surface of inspection apparatus 106. For example, an interference fit between an outer surface of inspection apparatus 106 an inner periphery of first seal 124 can compress first seal 124. Thus, where first seal 124 is an O-ring and inspection apparatus 106 includes a tube of a borescope, an inner diameter of first seal 124 can be smaller than an outer diameter of the portion of inspection apparatus 106 inserted into main passage 116 to produce an interference fit. In embodiments, first seal 124 also allows inspection apparatus 106 to move relative to first seal 124. The particular amount by which the sizes of first seal 124 and inspection apparatus 106 should differ to achieve a fluid-tight seal while allowing motion of inspection apparatus 106 relative to first seal 124 can be determined by one of ordinary skill in the art based on the particular implementation of guide system 100 and/or properties of fluids and/or materials used and/or encountered therein.

A retainer 134 can be mounted in outboard portion 114 of housing 110, farther from casing 12 than valve body 118 and first seal 124 are, and can selectively sealingly engage and/or retain inspection apparatus 106 against motion relative to retainer 134. In embodiments, retainer 134 can take the form of a modified sealing gland or gland seal. Such a sealing gland typically includes a substantially cylindrical body with a bore therethrough, the bore narrowing so that the body has an internal shoulder. A sealant, such as a cylindrical or annular member of elastomer, is mounted in the wider part of the bore and engages the shoulder, either directly or via a seat. A threaded cap engaging threads on the body can then be rotated to compress the sealant against the shoulder or the seat and to seal the passage. A follower can be included between the cap and the sealant and can be mounted to slide in response to action of the cap, but to be restrained against rotation.

In embodiments of the invention, retainer 134 can include a second seal 128 arranged to selectively sealingly engage inspection apparatus and to selectively retain inspection apparatus against motion relative to second seal 128 responsive to an actuator 140. Actuator 140 can shift second seal 128 between and/or induce a relaxed state 130 (FIGS. 2-4) in which second seal 128 at least allows inspection apparatus 106 to move relative to second seal 128, and a retention state 132 (FIG. 5) in which second seal 128 sealingly engages inspection apparatus 106 and retains inspection apparatus against motion relative to second seal 128. In the example shown in FIGS. 2-5, second seal 128 can be a substantially annular member in mechanical communication with actuator 140. Second seal 128 can be made of an elastomeric material or other deformable material with at least a degree of shape memory as is known in the art so that second seal 128 will tend to return to its initial shape after having been deformed, such as by being compressed and then having compression force/pressure removed. Main passage 116 can widen in outer portion 114 of housing 110 so that housing 110 includes a shoulder 146. In the example shown, second seal 128 is arranged between actuator 140 and shoulder 146, and actuator 140 can move toward shoulder 146, forcing second seal 128 into engagement with and/or compressing second seal 128 against shoulder 146. For example, actuator 140 can be a substantially annular member including external threads 141, and housing 110 can include corresponding threads 136 on an internal surface 138 of outboard portion 119 of main passage 116 so that rotation of actuator 140 in a first direction 142 can cause actuator 140 to move toward shoulder 146, while rotation of actuator 140 in a second direction 144 can cause actuator 140 to move away from shoulder 146. In addition, an intermediate member 145, such as a washer or other suitable substantially annular member, can be placed between actuator 140 and second seal 128, such as to reduce shear forces experienced by second seal 128 as a result of rotation of actuator 140.

In the example of FIGS. 2-5, therefore, in terms of sealing glands or gland seals, second seal 128 can act as a sealant, actuator 140 can act as a cap, intermediate member 145 can act as a follower, and housing 110 can act as a body. It should be noted that intermediate member 145, while not described as being non-rotatable, could easily be so modified by one of ordinary skill in the art, such as by including a projection on an outer periphery of intermediate member 145 that slides in an axial groove in housing 110 on internal surface 126 of main passage 116, or any other suitable arrangement. In addition, while second seal 128, actuator 140, and intermediate member 145 have been shown and/or described as substantially annular, any other suitable shape could be used so long as retainer 134 allows inspection apparatus 106 to be inserted through main passage 116 and can provide sealing engagement and retention of inspection apparatus 106 when desired. While no seat has been specifically described, the addition and use of such a seat is well within the purview of one of ordinary skill in the art, particularly where environmental conditions and/or material properties may be better handled by using a seat between second seal 128 and shoulder 146.

With particular reference to FIGS. 4-5, operation of retainer 134 can start with second seal 128 in relaxed state 130. Actuator 140 can be rotated to move toward shoulder 146 until second seal 128 engages shoulder 146, at which point second seal 128 can deform due to compression as actuator 140 continues to move toward shoulder 146. It should be noted that second seal 128 could already be in engagement with shoulder 146 so that actuator 146 would simply begin and/or continue compression of second seal 128 when rotated in first direction 142. As a result of the geometry of housing 110, shoulder 146, actuator 140/intermediate member 145, and second seal 128, and of compression induced by rotation of actuator 140 in first direction 142, second seal 128 deforms so that a thickness of second seal 128 decreases, and material of second seal 128 moves so that an inner diameter of second seal 128 also decreases in size. When inspection apparatus 106 extends through second seal 128, with particular reference to FIG. 5, an inner periphery of second seal 128 can engage an outer surface of inspection apparatus 106 and exert pressure on inspection apparatus 106 that can increase as actuator 140 continues to move toward shoulder 146. Thus, as pressure increases, second seal 128 can sealingly engage inspection apparatus 106, and eventually the pressure can reach a point at which, because of an ever-increasing coefficient of static friction between second seal 128 and inspection apparatus 106, relative motion between second seal 128 and inspection apparatus 106 can be substantially prevented. Since the inner periphery of second seal 128 would continue to decrease if inspection apparatus 106 were not present, the deformation of second seal 128 can create an interference fit between inspection apparatus 106 and the inner periphery of second seal 128. Thus, due to compression of second seal 128, second seal 128 can retain inspection apparatus 106 against motion relative to second seal 128, such as in an interference fit, and actuator 140 can induce second seal 128 to occupy the retention state 132. By rotating actuator 140 in second direction 144, compression of second seal 128 can be eased until it assumes the relaxed state 130, in which inspection apparatus 106 can move relative to second seal 128 and/or second seal 128 can disengage from inspection apparatus 106.

Use of the first example of guide system 100 can be illustrated with reference to FIGS. 2-5. With initial reference to FIGS. 2 and 3, in which valve body 118 occupies first position 120, inspection apparatus 106 can be inserted so that its end is between first seal 124 and valve body 118. In this state, first seal 124 can engage inspection apparatus 106 and can prevent passage of fluid in either direction in main passage 116. Turning to FIG. 4, with inspection apparatus 106 engaged by first seal 124, valve body 118 can be moved to second position 122 so that inspection apparatus 106 can be extended through the remainder of main passage 116 and into casing 12. In embodiments including guide conduit 200, inspection apparatus 106 can be extended into guide conduit 200 within casing 12. Continuing to FIG. 5, when the end of inspection apparatus 106 has reached a desired inspection site 202, retainer 134 can be engaged, such as by rotating threaded member 140 in first direction 142 until second seal 128 sealingly engages inspection apparatus 106 and retains inspection apparatus 106 against movement relative to second seal 128 as described above. It should be noted that there may be an intermediate state in which second seal 128 sealingly engages inspection apparatus 106, but allows motion of inspection apparatus 106 relative to second seal 128 in a fashion similar to the action of first seal 124.

When inspection apparatus 106 is to be moved to another inspection site 202 or removed from guide system 100, guide system 100 can be returned to a state similar to that shown in FIG. 4. Thus, retainer 134 can be disengaged, such as by rotating threaded member 140 to allow second seal 128 to relax at least enough to allow movement of inspection apparatus 106 relative thereto, and inspection apparatus 106 can be withdrawn enough to allow navigation to another inspection site 202, at which point guide system 100 can be returned to a state similar to that shown in FIG. 5. Alternatively, after retainer 134 is disengaged, guide system 100 can be returned to a state similar to that shown in FIG. 3, such as by withdrawing inspection apparatus 106 so that its end is between first seal 124 and valve body 118, and by placing valve body 118 in first position 120 to seal outboard portion 119 of main passage 116 from fluid communication with interior 16 of casing 12. Once valve body 118 is in first position 120, inspection apparatus 106 can be removed.

Figure 6:
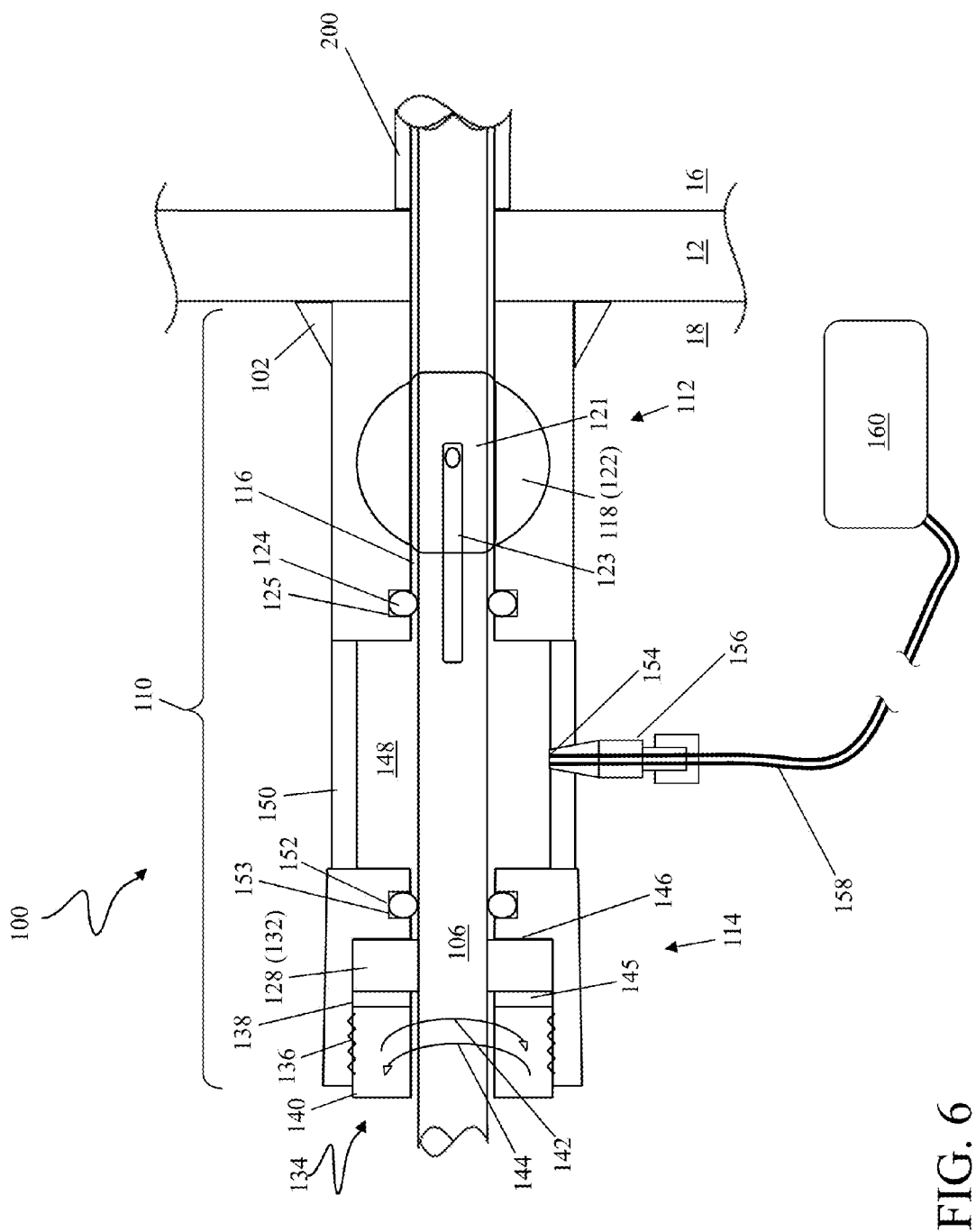
FIG. 6 shows a schematic cross sectional diagram of a second example of an inspection apparatus guide system according to embodiments of the invention disclosed herein in a state similar to the fourth state of the first example.

As seen in a second example of guide system 100 depicted in FIG. 6, a selectively pressurized chamber 148 can be included in housing 110 between valve body 118 and retainer 134. For example, where housing 110 is substantially cylindrical, a substantially annular wall 150 can extend between first seal 124 and retainer 134, effectively defining chamber 148 as a widened portion of main passage 116. A third seal 152 can be included between retainer 134 and chamber 148, particularly between shoulder 146 and chamber 148, and can be substantially identical to first seal 124 in form, support, and function. For example, third seal 152 can be an O-ring mounted in a substantially annular groove 153 of housing 110 on an internal surface 126 of main passage 116. Chamber 148 can be filled with a fluid through port 154, which can selectively be placed in fluid communication with a fluid reservoir 160, such as by a valve 156 and/or a conduit 158.

During insertion of inspection apparatus 106, once the end of inspection apparatus 106 has passed first seal 124, so that both first seal 124 and third seal 152 sealingly engage inspection apparatus 106, chamber 148 can be filled with fluid from reservoir 160 before valve body 118 is moved to second position 122. Particularly when chamber 148 is filled with fluid under pressure, passage of fluid from interior 16 of casing 12 into outboard portion 119 (FIG. 2) of main passage 116 can be even further reduced and/or more easily prevented. With proper selection of fluid with which to fill chamber 148, contamination of casing interior 16 from ambient air can be substantially prevented, and chemical properties of the fluid in casing 12 that might be construed as undesirable can be dampened and/or nullified. For example, where casing 12 is filled with pressurized hydrogen, filling chamber 148 with pressurized nitrogen can dampen effects of hydrogen's chemical properties should any hydrogen manage to pass first seal 124, and because chamber 148 is pressurized, ambient air is very unlikely to be able to enter chamber 148, inner portion 117 (FIG. 2) of main passage 116, and/or casing interior 16, reducing likelihood of contamination of interior 16. Similarly, when chamber 148 is pressurized, hydrogen from casing interior 16 is less likely to enter chamber 148, reducing leakage of hydrogen from casing 12. Moving/Removing inspection apparatus 106 can be done in much the same way as described with respect to the first example shown in FIGS. 2-5, but with the option of emptying chamber 148 after valve body 118 is moved to first position 120.

Figure 7:
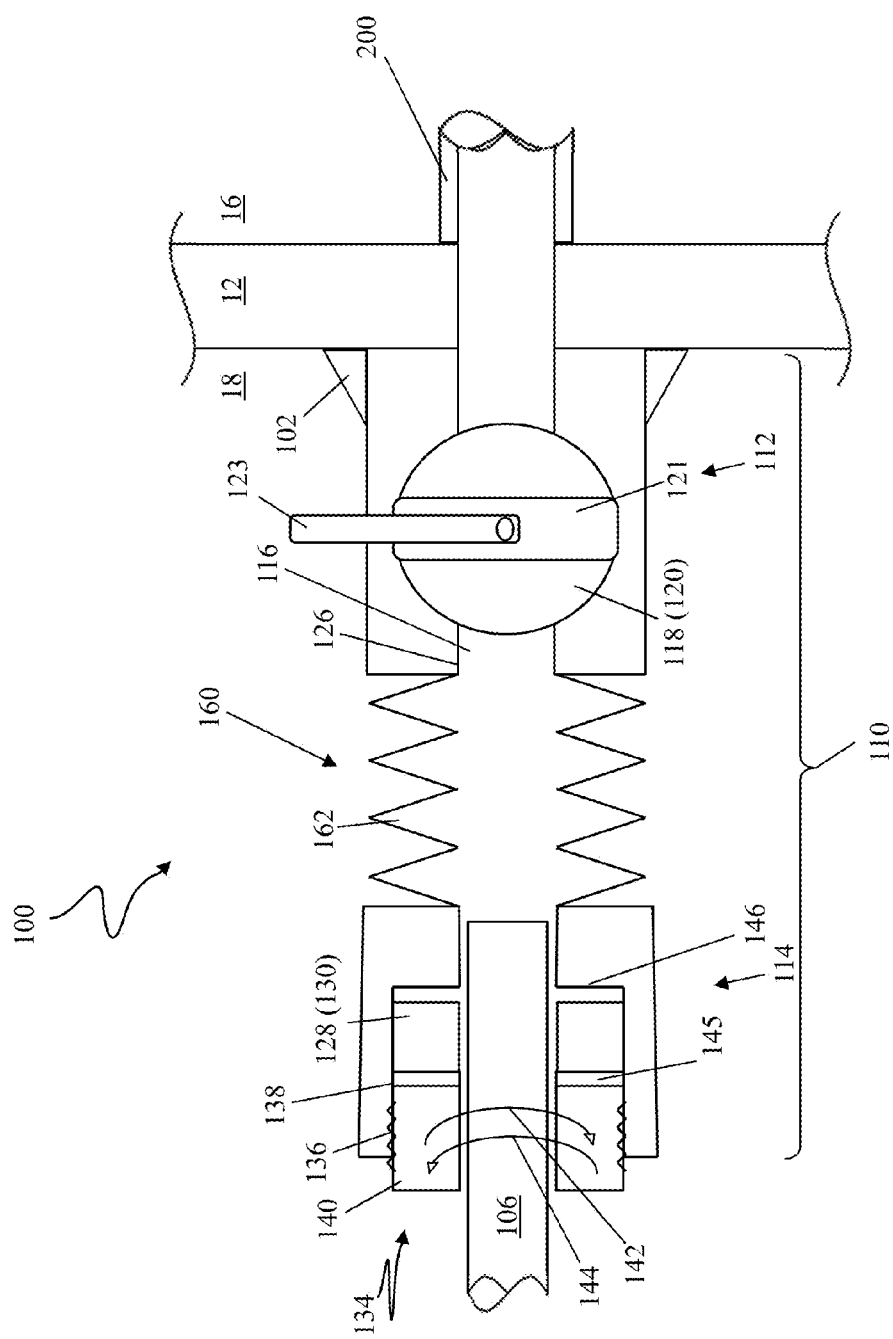
FIG. 7 shows a schematic cross sectional diagram of a third example of an inspection apparatus guide system according to embodiments of the invention disclosed herein in a first state.
Figure 8:
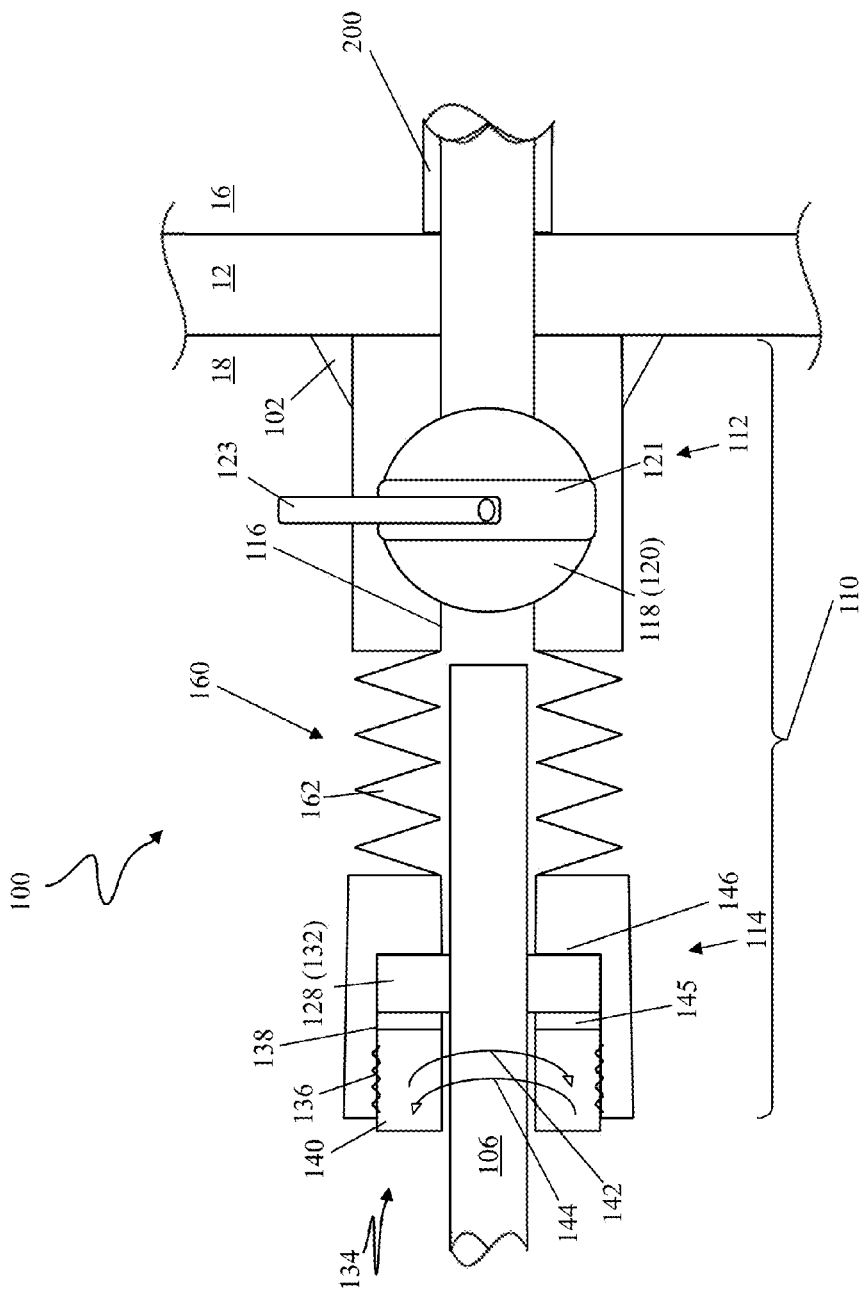
FIG. 8 shows a schematic cross sectional diagram of the third example of an inspection apparatus guide system according to embodiments of the invention disclosed herein in a second state.
Figure 9:
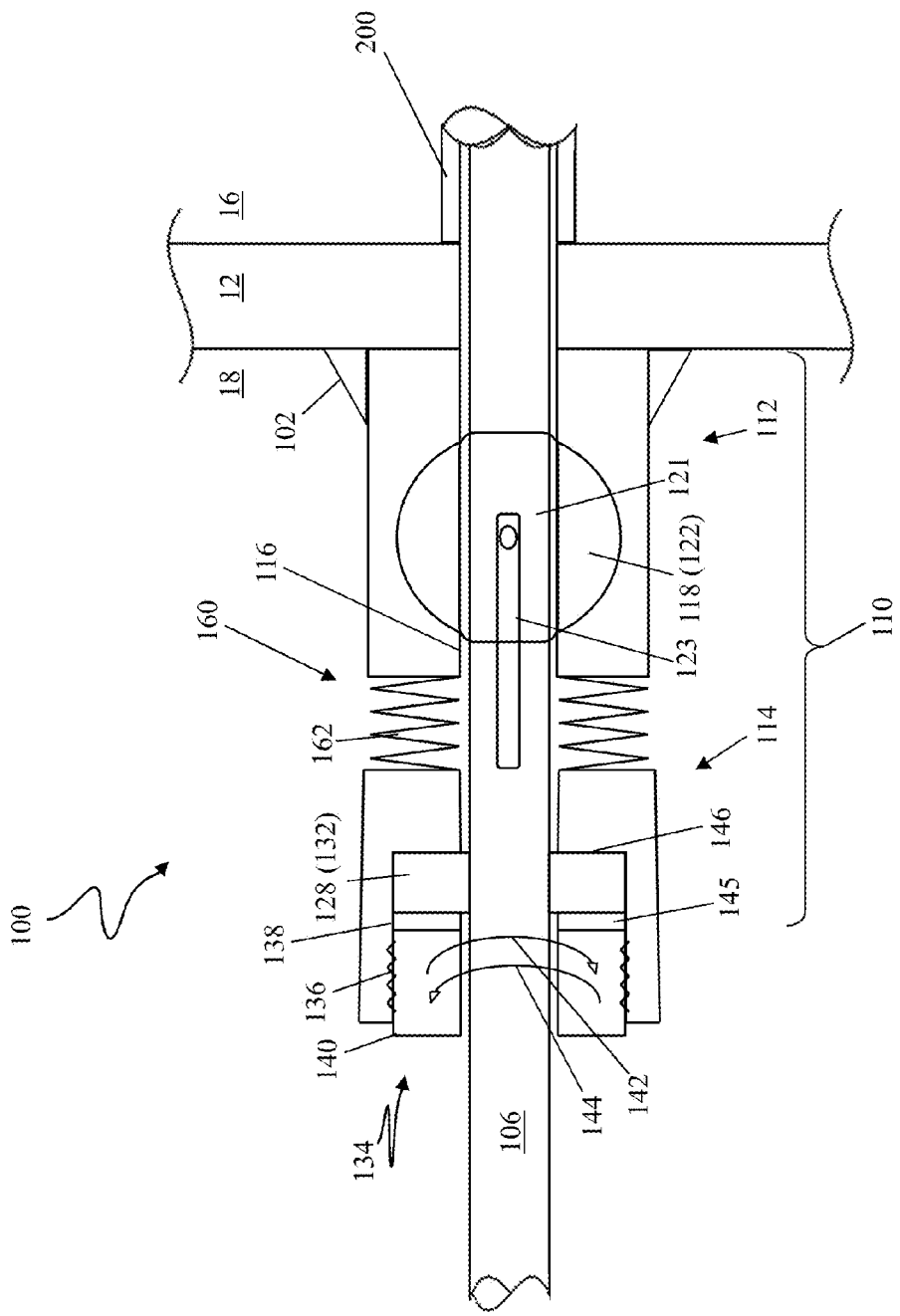
FIG. 9 shows a schematic cross sectional diagram of the third example of an inspection apparatus guide system according to embodiments of the invention disclosed herein in a third state.

A third example of a guide system 100 according to embodiments of the invention is seen in FIGS. 7-9 and can include a selectively collapsible portion 160 of housing 110 between valve body 118 and retainer 134. For example, collapsible portion can include a bellows arrangement 162, or the like, which can be formed from an articulated tube, sequential discs alternately connected at outer and inner peripheries, and/or other suitable arrangement as may be known in the art. Bellows 162 can be made from, as non-limiting examples, a resinous material, a plastic material, metal, a metal alloy, a composite material, and/or any other material and/or combination of materials deemed suitable and desirable for use in embodiments. Because of the location of collapsible portion 160, first seal 124 need not be included, though it could be included in housing 110 outboard of collapsible portion 160, similar to the location of third seal 152 in the last example seen in FIG. 6.

In use, referring to FIG. 7, with valve body 128 in first position 120 and collapsible portion 160 extended to substantially its full length or to at least a functional full length of inspection apparatus 106, inspection apparatus 106 can be inserted through retainer 134 until, as seen in FIG. 8, the end of inspection apparatus 106 is near an inboard end of collapsible portion 160 and/or near valve body 118. Retainer 134 can be used so that second seal 128 sealingly engages and retains inspection apparatus 106 against motion relative to second seal 128, at which point valve body 118 can be moved to second position 122, as seen in FIG. 9. While some fluid from interior 16 may enter collapsible portion 160, a total volume thereof relative to that of interior 16 should be negligible and therefore acceptable. However, first seal 124 and/or third seal 152 can be included on either end of collapsible portion 160 in a fashion similar to that seen in the example of FIG. 6 to reduce fluid movement between interior 16 and outboard portion 119 (FIG. 2) of main passage 116. As also seen in FIG. 9, as inspection apparatus 106 is inserted into casing 12, retainer 134 travels with inspection apparatus 106, which collapses collapsible portion 160. To move or remove inspection apparatus 106, retainer 134 and inspection apparatus 106 can be moved away from/out of casing 12, extending collapsible portion 160, until a desired branch point 206 is reached and/or until the end of inspection apparatus 106 passes valve body 118. To continue removal of inspection apparatus 106, once the end of inspection apparatus 106 is inboard of valve body 118, valve body 118 can be moved to first position 120, retainer 134 can be disengaged, and inspection apparatus 106 can be pulled out of retainer 134 and guide system 100. Any fluid that may have occupied collapsible portion 160 can generally be vented, though embodiments can include any known reclamation and/or disposal method if deemed necessary and/or suitable.

As discussed above, guide conduit 200 in casing interior 16 can be aligned with first through hole 14 and can extend from first through hole 14 to an inspection site 202. As also discussed above, branch conduit(s) 204 can extend from a branch point 206 to one or more inspection sites 202. In embodiments, guide conduit 200 and/or branches 204 and/or branch points 206 are installed during an evacuated state of machine 10, which can include initial manufacture of machine 10. In addition, installation can be performed when machine 10 is in a disassembled state, since placement and mounting of guide conduit 200 and/or branches 204 and/or branch points 206 through an access port or the like would be extremely difficult. Similarly, housing 110 can be attached to casing 12 during an evacuated state of machine 10, which can include initial manufacture, to avoid excessive leakage and/or contamination of fluid from casing interior 16.

Figure 10:
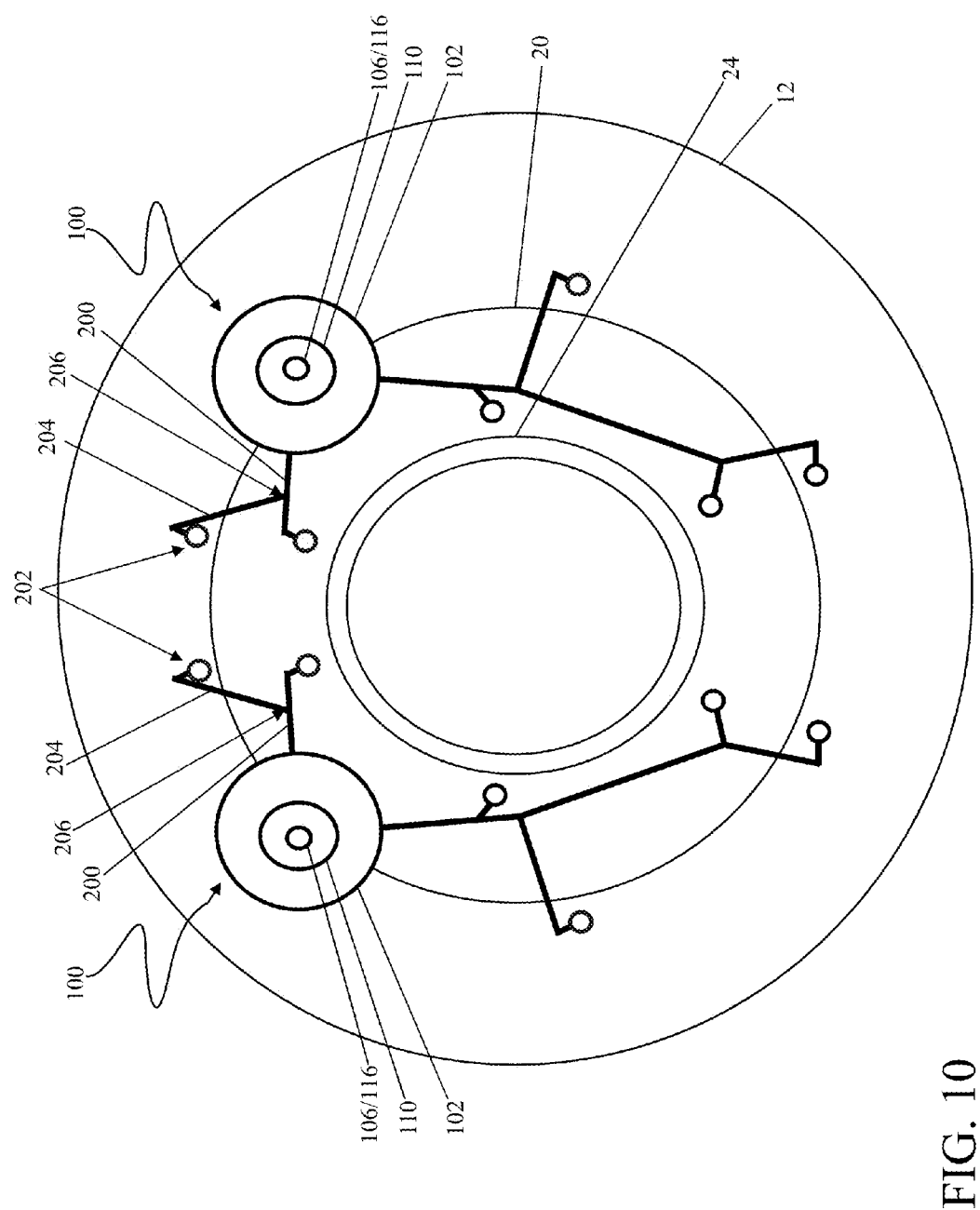
FIG. 10 shows a schematic transverse cross sectional diagram of a machine with which an inspection apparatus guide system according to embodiments of the invention disclosed herein can be implemented.
Figure 11:
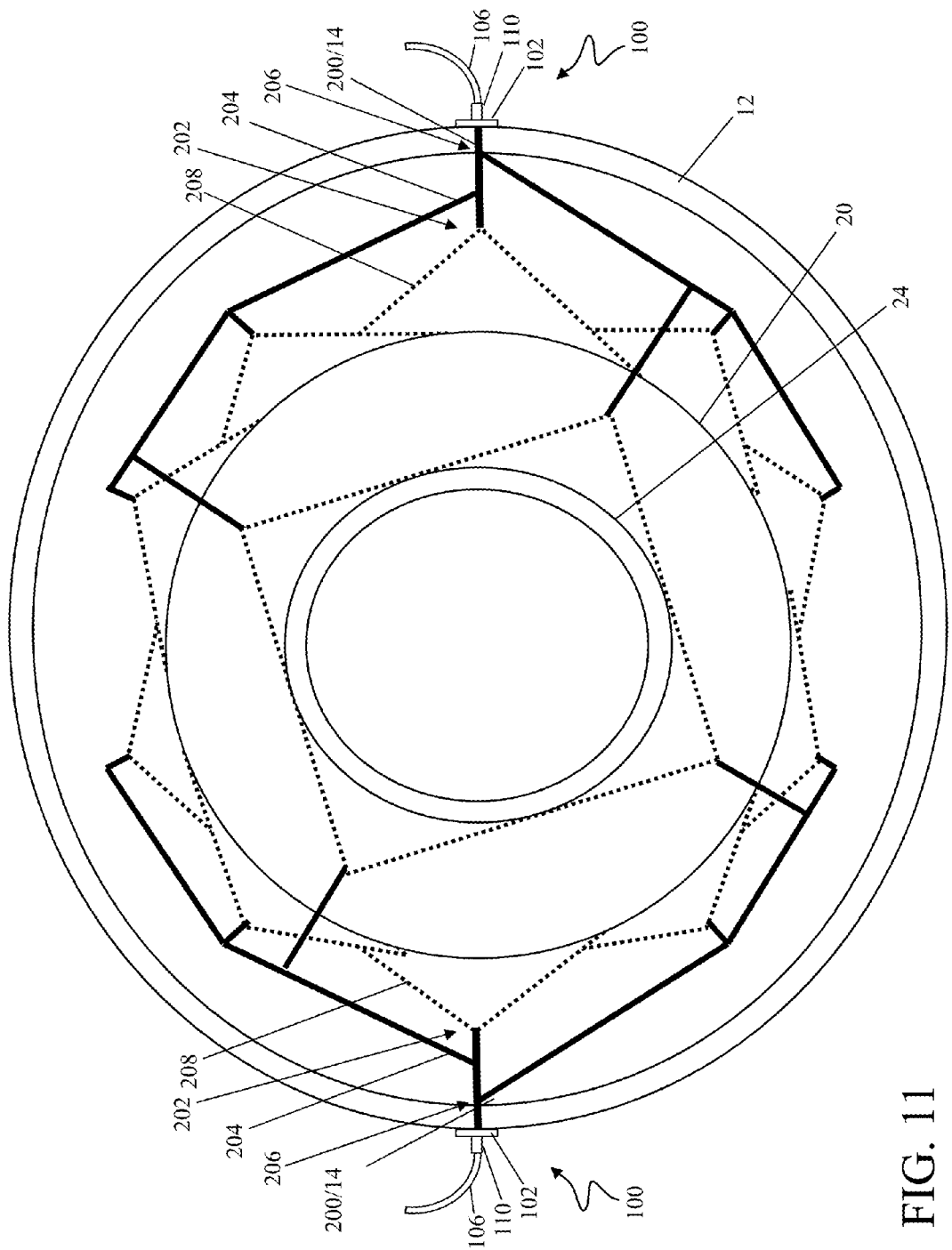
FIG. 11 shows a schematic transverse cross sectional diagram of a machine with which an inspection apparatus guide system according to embodiments of the invention disclosed herein can be implemented.

Some examples of implementations of guide conduit 200, branches 204, and/or branch points 206 can be seen schematically in FIGS. 10 and 11. By using branch points 206 within casing 12, and corresponding branches or branch conduits 204, multiple predetermined inspection points 202 can be reached from a single guide system housing 110. In addition, as particularly seen in FIG. 11, each inspection point 202 can provide a respective field of view 208, and, by suitable positioning of predetermined inspection points 202, an entire part or region in casing 12 can be viewed during an inspection. For example, an entire circumference of end windings and/or a rotor assembly could be inspected with appropriate number and location of inspection sites 202.

Figure 12:
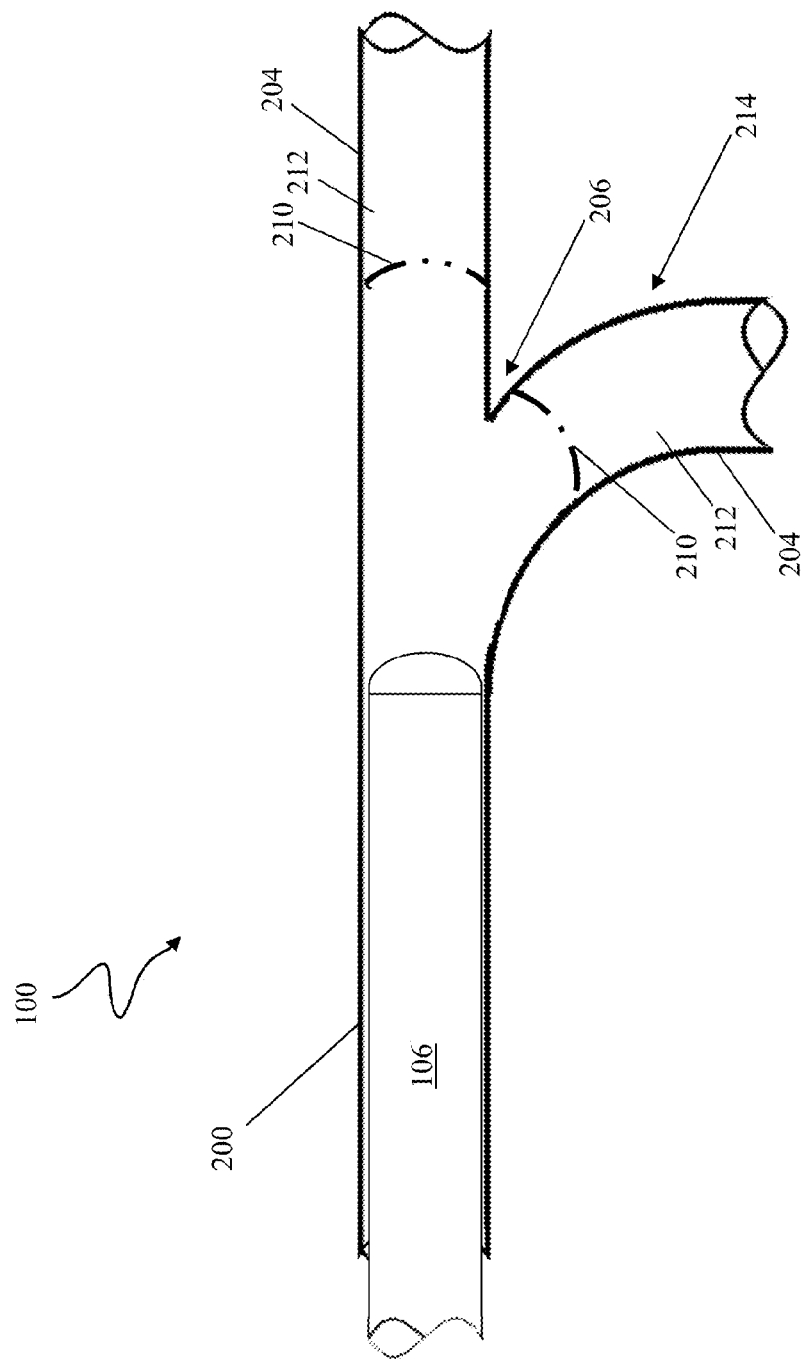
FIG. 12 shows a detailed schematic cross sectional view of an element of embodiments of the invention disclosed herein.

As mentioned above, and as seen schematically in FIG. 12, a guide mark 210 can be formed on an internal surface 212 of each branch conduit 204 extending from a branch point 206 to assist with navigation within guide conduit(s) 200, 204 to inspection sites 202. Each guide mark 210 can provide identification of an associated branch conduit 204. For example, as seen in FIG. 12, a first guide mark 210 can include a single dot between two dashes, while a second guide mark 210 can include two dots between two dashes, thereby identifying a respective branch conduit 204 in which each guide mark 210 appears. While a pattern of dots and dashes is shown in FIG. 12, it should be readily apparent that any type of marking could be used for guide mark(s) 210, including, but not limited to, a pattern, an image, text, color, engraving or other removal of material from the internal surface of a given conduit, attachment of material to the internal surface of a given conduit, and/or any combination of these and/or any other suitable means of making a guide mark 210 so that each guide mark 210 can convey which branch conduit 204 it identifies.

As also illustrated in FIG. 12, branch point 206 and/or one or more branches 204 can include a rounded bend or a curve 214. A typical inspection apparatus 106 can include hardware enabling selective, controlled bending and/or articulation of inspection apparatus 106 and/or an end portion thereof. However, inspection apparatus 106 may not include enough control and/or may not include any hardware to control articulation and/or bending, particularly of an end portion. Including a rounded bend 214 as illustrated in FIG. 12 can enable apparatus without such hardware to navigate guide conduit 200 and its branches 204. A curved portion, such as bend 214, of a branch 204 and/or branch point 206 can also make it easier for apparatus with control of articulation and/or bending, particularly of an end portion, to navigate guide conduit 200 and its branches 204.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. An inspection apparatus guide system comprising:
a housing configured at a first end thereof for attachment to a casing, the housing including a main passage therethrough configured for communication with a first through hole in the casing, the main passage being sized to receive an inspection apparatus extendible therethrough;
a guide conduit positioned in the casing and substantially aligned with the first through hole, the guide conduit including:
a branch point positioned within the casing; and
at least two branch conduits formed by and extending from the branch point, the at least two branch conduits in communication with one another and extending to respective inspection sites inside the casing;
a valve body mounted in the housing so that an outboard portion of the main passage lies between the valve body and a second end of the housing, the valve body having a first position in which the valve body seals the outboard portion of the main passage from the interior of the casing, the valve body further having a second position in which the valve body opens the main passage to the interior of the casing;
a first seal mounted in the housing so as to project into the main passage farther from the casing than the valve body is with an inner periphery of the first seal that is smaller than an outer periphery of the inspection apparatus so that the first seal is arranged to sealingly engage the inspection apparatus, thereby substantially preventing passage of fluid between the inner periphery of the first seal and the outer periphery of the inspection apparatus; and
a retainer mounted within the housing and surrounding a portion of the outboard portion of the main passage, the retainer including:
a second seal; and
an actuator in mechanical communication with the second seal, the actuator configured to induce the second seal to shift between:
a retention state in which the second seal sealingly engages and retains the inspection apparatus against motion; and
a relaxed state in which the second seal allows the inspection apparatus to move.

2. The inspection apparatus guide system of claim 1, further comprising at least one guide mark on an internal surface of the guide conduit near the branch point, each guide mark identifying one of the branch point or a respective branch conduit of the at least two branch conduits of the guide conduit.

3. The inspection apparatus guide system of claim 1, wherein the retainer mounted in the housing is positioned farther from the valve body than the first seal is.

4. The inspection apparatus guide system of claim 1, wherein the housing includes an internal shoulder farther from the casing than the first seal is, an inner diameter of the main passage is smaller on an inboard side of the shoulder than on an outboard side of the shoulder, the second seal includes a substantially annular compression member configured to engage the shoulder, the housing includes threads on an internal surface of the main passage outboard of the shoulder, and the actuator includes a threaded member including external threads that interact with the threads on the internal surface of the main passage so that rotation of the threaded member in a first direction moves the threaded member toward the shoulder and rotation of the threaded member in a second direction moves the threaded member away from the shoulder.

5. The inspection apparatus guide system of claim 1, further comprising a selectively pressurized chamber in the main passage farther from the valve body than the first seal is, the selectively pressurized chamber including a port through a wall of the chamber and a valve connected to the port and to a source of pressurized fluid.

6. The inspection apparatus guide system of claim 5, further comprising a third seal in the main passage farther from the valve body than the selectively pressurized chamber is, and the first and third seals allow motion of the inspection apparatus relative to the first and third seals.

7. The inspection apparatus guide system of claim 1, wherein the first through hole of the sealed casing is an access port of the sealed casing and the housing is configured to sealingly attach to the sealed casing over the access port.

8. The inspection apparatus guide system of claim 1, wherein the inspection apparatus is a flexible borescope.

9. An inspection apparatus guide system for facilitating inspection of an interior of a sealed casing of a machine, the inspection system comprising:
a guide conduit positioned below a first through hole in the sealed casing and including a diameter substantially equal to a diameter of the first through hole, the guide conduit including:
a branch point positioned within the sealed casing; and
at least two branch conduits formed by and extending from the branch point, the at least two branch conduits in communication with one another and extending to respective inspection sites inside the casing;
a housing including a main passage therethrough sized to allow passage of the inspection apparatus, the housing being configured for attachment to the sealed casing to align at least an inboard end of the main passage with the first through hole and with an end of the guide conduit;

a valve body supported in the housing so as to at least span the main passage and having a first position that substantially prevents fluid communication between an interior of the sealed casing and a portion of the main passage outboard of the valve body, and having a second position that allows fluid communication between the interior of the sealed casing and the portion of the main passage outboard of the valve body; and a first seal supported in the housing outboard of the valve body and projecting into the main passage, the first seal having an inner periphery that is smaller than an outer periphery of the inspection apparatus and being arranged to engage the inspection apparatus in an interference fit when the inspection apparatus extends through the main passage, wherein the housing and the first seal are configured to prevent a fluid of the sealed casing from flowing to an exterior of the sealed casing from the housing.

10. The inspection apparatus guide system of claim 9, wherein the main passage includes a second seal mounted between the first seal and the valve body.

11. The inspection apparatus guide system of claim 9, wherein the main passage includes a selectively pressurized chamber between the first seal and the second seal.

12. The inspection apparatus guide system of claim 9, further comprising at least two guide marks on an internal surface of the guide conduit near the branch point, each guide mark identifying a respective branch conduit of the at least two branch conduits extending from the branch point.

13. An inspection apparatus guide system for facilitating inspection of a sealed casing of a machine, the inspection apparatus guide system comprising:

a housing including a main passage configured to allow passage of an inspection apparatus selectively extendible therethrough;

a guide conduit positioned in the sealed casing and substantially aligned with the main passage of the housing, the guide conduit including:
  a branch point positioned within the casing; and
  at least two branch conduits formed by and extending from the branch point, the at least two branch conduits in communication with one another and extending to respective inspection sites inside the casing;

a retainer mounted in the housing at an outboard end of the housing opposite the inboard end, the retainer being configured to selectively engage the inspection apparatus in an interference fit and to selectively retain the inspection apparatus against motion relative to the retainer; and a valve body supported in the housing so as to seal an outboard portion of the main passage between the valve body and the outboard end of the housing against fluid communication with an interior of the sealed casing in a first position of the valve body and to open the outboard portion of the main passage to fluid communication with the interior of the casing in a second position of the valve body.

14. The inspection apparatus guide system of claim 13, further comprising at least one seal in the main passage between the valve body and the retainer, each of the at least one seal being configured to engage the inspection apparatus in an interference fit and to allow motion of the inspection apparatus relative to the respective seal.

15. The inspection apparatus guide system of claim 13, wherein the retainer includes a substantially annular member selectively engaging a shoulder of the housing in the main passage and an actuator configured to selectively move the substantially annular member between a retention state, in which the inspection apparatus is engaged in an interference fit with the substantially annular member and is retained against motion relative to the retainer, and a relaxed state, in which the inspection apparatus can move relative to the retainer.

* * * * *